United States Patent [19]

Alig et al.

[11] Patent Number: 5,064,863

[45] Date of Patent: Nov. 12, 1991

[54] PHENOXYPROPANOLAMINES AND PHARMACEUTICAL USE

[75] Inventors: Leo Alig, Kaiseraugst; Marcel Müller, Frenkendorf, both of Switzerland

[73] Assignee: Hoffmann-La Roche Inc., Nutley, N.J.

[21] Appl. No.: 130,929

[22] Filed: Dec. 10, 1987

Related U.S. Application Data

[63] Continuation of Ser. No. 659,791, Oct. 11, 1984, abandoned.

[30] Foreign Application Priority Data

Oct. 19, 1983 [CH] Switzerland ............ 4684/83
Sep. 7, 1984 [CH] Switzerland ............ 4288/84

[51] Int. Cl.$^5$ ............ A61K 31/135; C07C 217/72
[52] U.S. Cl. ............ 514/653; 514/255; 514/438; 514/532; 514/546; 514/603; 544/394; 544/399; 544/400; 544/401; 549/70; 549/71; 549/72; 549/73; 549/75; 549/77; 560/105; 560/252; 564/86; 564/349
[58] Field of Search ............ 549/70, 71, 72, 73, 549/75, 77; 560/105, 252; 564/86, 349; 544/394, 399, 400, 401; 514/255, 438, 532, 546, 603, 653

[56] References Cited

U.S. PATENT DOCUMENTS

| | | | |
|---|---|---|---|
| 3,501,769 | 3/1970 | Crowther et al. | 564/349 X |
| 3,723,476 | 3/1973 | Nakanishi et al. | 564/349 X |
| 3,723,524 | 3/1973 | Augstein et al. | 564/349 X |
| 3,892,799 | 7/1975 | Pinno | 564/349 X |
| 4,127,675 | 11/1978 | Murakami et al. | 564/349 X |
| 4,161,542 | 7/1979 | Carlsson et al. | 564/349 X |
| 4,165,384 | 8/1979 | Carlsson et al. | 564/349 X |
| 4,171,370 | 10/1979 | Jones et al. | 564/349 X |
| 4,252,984 | 2/1981 | Mandury et al. | 564/349 X |
| 4,263,325 | 4/1981 | Carlsson et al. | 564/349 X |
| 4,336,267 | 6/1982 | Carlsson et al. | 564/349 X |
| 4,358,460 | 11/1982 | Cohen | 564/349 X |
| 4,382,958 | 8/1983 | Duckworth | 564/653 |
| 4,585,796 | 4/1986 | Plig et al. | 564/349 X |
| 4,649,160 | 3/1987 | Machin | 564/349 X |
| 4,816,604 | 3/1989 | Louis et al. | 564/349 X |

FOREIGN PATENT DOCUMENTS

| | | |
|---|---|---|
| 0170121 | 2/1986 | European Pat. Off. ............ 564/349 |
| 2503222 | 7/1976 | Fed. Rep. of Germany ...... 564/345 |
| 8305687 | 2/1984 | South Africa . | |

OTHER PUBLICATIONS

Wolff, "Burger's Medicinal Chemistry", Part III, 4th ed., p. 311 (1981).
Derwent 58932B-(J5 4081-234) 1977.
Derwent 03841C-(EP 6-614) 1978.
Derwent 05881c-(EP 7-294) 1978.
Derwent 09583C-(EP 7.605) 1978.
Derwent 71844C-(DT 3010-752) 1979.
Derwent 34305D-(US 4,236,325) 1977.
Derwent 22,618-(BEL 675,967) 1966.
Derwent 27,928-(BE 692,309) 1967.
Derwent 36,501-(NE 68 12681) 1969.
Derwent 41,137-(FR 7255M) 1969.
Derwent 14032A-(BF 857-928) 1976.
Derwent 68932A-(BE 865-201) 1977.
Derwent 13,219-(Can. 692,054) 1964.
Derwent 15,538-(NE 6,408,111) 1965.
Derwent 16,090-(NE 6,410,522) 1965.
Derwent 16,563-(FR 1,394,771) 1965.
Derwent 18,113-(US 3,203,992) 1965.
Derwent 21,447-(EIRE 331/66) 1966.
Derwent 05882E-(BE 889-515) 1980.

(List continued on next page.)

Primary Examiner—Richard L. Raymond
Attorney, Agent, or Firm—George M. Gould; Bernard S. Leon; William G. Isgro

[57] ABSTRACT

Tertiary and secondary amines of the formulas

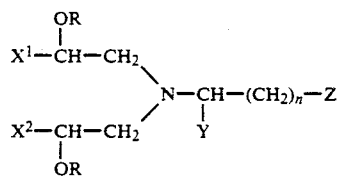

and

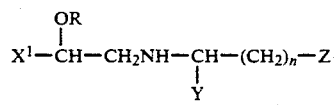

wherein
n is the integer 1 or 2, p0 R is hydrogen, lower-alkanoyl or phenyl-lower-alkanoyl,
$X^1$ is phenoxymethyl optionally mono-fluorinated or mono-chlorinated in the ortho-position,
$X^2$ is lower-alkyl, phenoxymethyl optionally mono-fluorinated or mono-chlorinated in the ortho-position or phenyl optionally monosubstituted by fluorine, chlorine, trifluoromethyl or lower-alkoxy,
Y is hydrogen or methyl, and
Z is a phenyl or thienyl residue substituted as hereinafter described, and the physiologically and pharmaceutically compatible salts are described. The compounds of formulas I and V-1 have catabolic activity and can be used for the treatment of obesity and diabetes mellitus or for the treatment of conditions which are associated with an increased protein breakdown, or as feed additives for fattening animals. The compounds of formulas I and V-1 can be prepared starting from corresponding primary amines.

11 Claims, No Drawings

OTHER PUBLICATIONS

Derwent 28637E–(US 4,321,398) 1981.
Derwent 82141R–(JA 034,315) 1969.
Derwent 35794R–(GB 68-054534) 1968.
Derwent 84541R–(GB 54534) 1970.
Derwent 41074S–(JA 095027) 1969.
Derwent 21817T–(GB 041355) 1968.
Derwent 42120T–(FR 046875) 1970.
Derwent 42121T–(BE 7769690) 1970.
Derwent 10074U–(GB 035480) 1971.
Derwent 18303U–(US 207,954) 1971.
Derwent 77484V–(BE 813,866) 1973.
Derwent 03624W–(US 3,587,873) 1974.
Derwent 33574W–(NL 7500-209) 1969.
Derwent 66006W–(FR 2254-324) 1973.
Derwent 36281X–(DT 2531-312) 1974.
Derwent 60037X–(DT 2503-222) 1975.
Derwent 11888Y–(J5-2000-234) 1975.
Derwent 73581Y–(J5 2105-137) 1976.
C.A. 94:174504Y (1981).
Merck Index 9th Edit., p. 884 (Ed. 1976).

PHENOXYPROPANOLAMINES AND PHARMACEUTICAL USE

This is a continuation of application Ser. No. 659,791 filed Oct. 11, 1984, now abandoned.

BRIEF SUMMARY OF THE INVENTION

The invention relates to tertiary and secondary amines of the formula

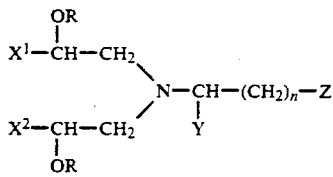

and

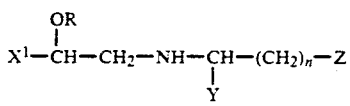

wherein
n is the integer 1 of 2,
R is hydrogen, lower-alkanoyl or phenyl-lower-alkanoyl,
$X^1$ is phenoxymethyl optionally mono-fluorinated or mono-chlorinated in the ortho-position,
$X^2$ is lower-alkyl, phenoxymethyl optionally mono-fluorinated or mono-chlorinated in the ortho-position or phenyl optionally monosubstituted by fluorine, chlorine, trifluoromethyl or lower-alkoxy,
Y is hydrogen or methyl, and
Z is a phenyl or thienyl residue substituted as hereinafter described,
and their physiologically compatible salts, prepared from the corresponding primary amines. The compound of formulas I and V-1 are useful in the treatment of obesity and diabetes mellitus or conditions which are associated with an increased protein breakdown, or as feed additives for fattening animals, have catabolic activity and can be used for the treatment of obesity and diabetes mellitus or for the treatment of conditions which are associated with an increased protein breakdown, or as feed additives for fattening animals. They are manufactured starting from corresponding primary amines.

DETAILED DESCRIPTION OF THE INVENTION

The present invention is concerned with novel phenoxypropanolamines, a process for their manufacture, novel intermediates therefor and pharmaceutical preparations based on these compounds.

The phenoxypropanolamines in accordance with the invention are compounds of the formula

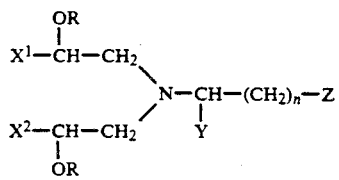

wherein
n is the integer 1 or 2,
R is hydrogen, lower-alkanoyl or phenyl-lower-alkanoyl,
$X^1$ is phenoxymethyl optionally mono-fluorinated or mono-chlorinated in the ortho-position,
$X^2$ is lower-alkyl, phenoxymethyl optionally mono-fluorinated or mono-chlorinated in the ortho-position or phenyl optionally monosubstituted by fluorine, chlorine, trifluoromethyl or lower-alkoxy,
Y is hydrogen or methyl,
Z is a group of the formula

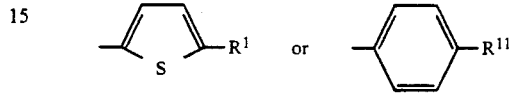

$R^1$ is optionally N-mono-lower-alkylated or N-di-lower-alkylated aminomethyl or a residue—$C(O)R^2$, —$C(R^3)=CH-(CH_2)_m-C(O)R^2$, —$C(H,R^3)-(CH_2)_{m+1}C(O)R^2$, —$C(H,R^3)-(CH_2)_p-OH$ or —$C(R^3)=CH-C(CH_3)=CH-COOCH_3$.
$R^{11}$ is hydroxy, lower-alkoxy, lower-alkanoyloxy, sulfamoyl, benzyloxy or phenoxy optionally ring-substituted by fluorine, chlorine, trifluoromethyl, lower alkyl or lower-alkoxy, or a group $R^1$, —O—$(CH_2)_q$—OH, —O—$(CH_2)_q$—$COOR^4$, —O—$(CH_2)_q$—O—$(CH_2)_r$—$R^5$ or

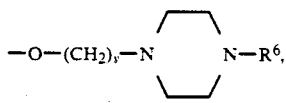

$R^2$ is hydroxy, lower-alkyl, lower-alkoxy, dimethylaminoethoxy, lower-alkoxycarbonylethyl or optionally mono-lower alkylated or di-lower alkylated amino,
$R^3$ is hydrogen or methyl,
$R^4$ is lower-alkyl,
$R^5$ is hydrogen, lower-alkyl or phenyl optionally para-substituted by chlorine, fluorine, trifluoromethyl, lower-alkyl or lower-alkoxy,
$R^6$ is lower-alkyl or phenyl optionally para-substituted by fluorine, chlorine, lower-alkyl or lower-alkoxy,
m and p are, independently, an integer of 0 to 6,
v is an integer of 2 to 4,
q and t are, independently, an integer of 1 to 6,
and physiologically compatible salts thereof.

The term "lower" used herein denotes residues with 1–6 carbon atoms, residues with 1–4 carbon atoms being preferred. Alkyl and alkoxy groups can be straight-chain or branched. Examples are methyl, ethyl, propyl, isopropyl, n-butyl and isobutyl and methoxy, ethoxy, propoxy, isopropoxy, butoxy and isobutoxy, respectively. Lower-alkanoyloxy residues are derived from lower-alkanecarboxylic acids such as formic acid, acetic acid, propionic acid and butyric acid.

The compounds of formula I, which lack a carboxyl group, form salts with acids, which are likewise an object of the invention. Examples of such salts are additional salts with physiologically compatible and pharmaceutically acceptable mineral acids such as hydrochloric acid, hydrobromic acid, sulfuric acid, phosphoric acid; or with organic acids such as methanesulphonic acid, acetic acid, propionic acid, citric acid, oxalic acid, succinic acid, malic acid, fumaric acid, phenylacetic acid or salicylic acid. Carboxylic acids of formula I can exist as salts. Examples of such salts are alkali metal, alkaline earth metal, ammonium and alkylammonium salts such as Na, K, Ca, trimethylammonium and ethanolammonium salts.

The compounds of formula I contain at least two asymmetric carbon atoms and can therefore exist as optically active enantiomers, as diastereomers or as racemates.

The compounds of formula I can be obtained in accordance with the invention by a) reacting an epoxide of the formula

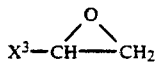

II or a β-keto halide of the formula $X^3-C(O)-CH_2-Hal$   III with a primary amine of the formula

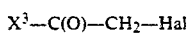

IV or a secondary amine of the formula

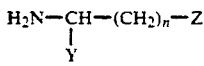

V wherein,
in formulas II-V n and Z are as previously described,
Hal is halogen, one of the groups $X^3$ and $X^4$ is a group $X^1$ and the other is a group $X^2$, whereby $X^3$ is a group $X^1$ when a compound of formula II or III is reacted with a compound of formula IV,
and reducing a $X^1-C(O)-$ or $X^2-C(O)-$ group present in a compound obtained to a $X^1-CHOH-$ or $X^2-CHOH-$ group, b) if desired, functionally modifying a reactive substituent present in group $X^1$, $X^2$, Y or Z of a compound of formula I, c) if desired, alkanoylating or phenalkanoylating the hydroxy groups present in a diol of formula I, and d) if desired, converting a compound of formula I into a salt.

The reaction of a compound of formula II with a compound of formula IV or V can be carried out in a manner known per se for the reaction of epoxides with amines to give aminoalcohols. The reaction partners are conveniently brought together in a suitable solvent and heated. As solvents there come into consideration inert organic solvents, e.g. dimethyl sulfoxide (DMSO), acetonitrile or ethers such as tetrahydrofuran (THF) or dioxane; or alcohols such as ethanol. The reaction temperature is not critical, the reaction being conveniently carried out at temperatures between 60° C. and the boiling point of the reaction mixture.

The reaction of a compound of formula III with a compound of formula IV or V can also be carried out in a manner known per se, conveniently in the presence of an aprotic solvent such as a halogenated hydrocarbon, for example, chloroform, at a temperature up to 200° C.

The compounds of the formula

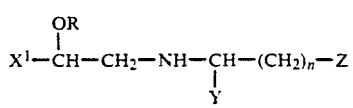

V-1 wherein $X^1$, R, Y, Z and n are as herein described, and their physiologically compatible salts form part of the invention. Furthermore, the invention is concerned with pharmaceutical preparations based on the compounds of formula V-1 as well as a process for the preparation of these compounds.

The compounds of formula V-1 can be obtained by
a) reacting an epoxide of the formula

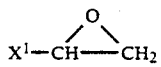

II-1 or a β-keto halide of the formula $X^1-C(O)-CH_2-Hal$   III-1 with an amine of formula IV, and reducing a $X^1-C(O)-$ group present in a compound obtained to the $X^1-CH(OH)-$ group, or b) reducing a compound of the formula

VI

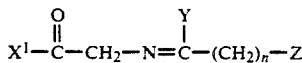

VII

VIII

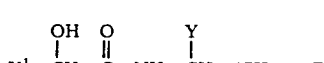

IX or

X c) if desired, functionally modifying reactive substituents present in group $X^1$, Y or Z of a compound of formula V-1, d) if desired, alkanoylating or phenalkanoylating the hydroxy group present in an alcohol of formula V-1, and e) if desired, converting a compound of formula V-1 into a salt, wherein in the previous formulas the residues $X^1$, Y, Z and n are as previously described.

The reaction of a compound of formula II-1 or III-1 with a compound of formula IV can be carried out in an inert organic solvent, conveniently, a protic solvent such as a lower alkanol, for example, ethanol. The reaction temperature is not critical, it can be in the range of from room temperature to the reflux temperature of the reaction mixture.

The reduction of a compound of formula VI can be carried out by catalytic hydrogenation, for example, in the presence of noble metal catalysts such as palladium or platinum catalysts or by treatment with a complex metal hydride such as sodium borohydride. The reaction conditions which are usually used for such reductions can be used in this case. The catalytic hydrogenation is conveniently carried out in an inert organic solvent such as a lower alkanol, for example, ethanol, at room temperature or a slightly elevated temperature, for example, at 20°–80° C. The reduction with a complex metal hydride is conveniently carried out in a lower alkanol, for example, methanol, at temperatures of 20°–30° C.

The compounds of formulas VII, VIII, IX and X can be reduced with a complex metal hydride in analogy to the compounds of formula VI. Sodium borohydride is a suitable complex metal hydride for the reduction of the compounds VII and VIII. The compounds IX are conveniently reduced with lithiumaluminumhydride.

In the case of the reaction of a compound III or III-1 with a compound IV or V resulting keto groups $X^1$—C(O)— or $X^2$—C(O)— can be reduced in a known manner to the secondary alcohol groups. This reduction can be carried out under the same conditions as for the reduction of the compounds VI–X described above, whereby the reduction with a complex metal hydride, especially sodiumborohydride, is preferred because of its selectivity.

A reactive substituent, especially a group —C(O)R$^2$ or —C(R$^3$)=CH—(CH$_2$)$_m$—C(O)R$^2$, in the thus-obtained reaction products of formula I or V-1 can be functionally modified. The esterification of a carboxyl group can be carried out in a manner known, for example, by means of an alkyl halide such as methyl iodide and a base. The saponification of an ester group is conveniently carried out under alkaline conditions, for example, by means of aqueous-alcoholic alkali hydroxide, for example, aqueous-methanolic potassium hydroxide. A double bond present in a side-chain R$^1$ or R$^{11}$ can be hydrogenated to a single bond for example, in the presence of a catalyst such as palladium-on-carbon in a solvent such as a lower alkanol, for example, ethanol. A hydroxy residue R$^{11}$ can be etherified in a known manner, for example, by reaction with a mesylate or halide corresponding to the ether residue and in the presence of a base such as potassium hydroxide in a solvent such as a lower alkanol, for example, n-propanol, or in the presence of potassium t-butylate in a solvent such as dimethylsulfoxide.

An optionally mono-lower alkylated or di-lower alkylated carbamoyl group R$^1$ or R$^{11}$ can be reduced to the corresponding aminomethyl group by reduction for example, with complex metal hydrides such as lithiumaluminumhydride. A lower-alkoxycarbonyl group can be reduced to the hydroxymethyl group in an analogous manner.

The alkanoylation or phenalkanoylation of the hydroxy groups present in the γ-position to the N-atom of a diol of formula I or of an alcohol of formula V-1 can be carried out in a known manner by means of the corresponding carboxylic acid or of a corresponding acid halide in the presence of a strong acid such as hydrochloric acid.

The compounds of formulas VI–X can be prepared in a known manner, for example, the compounds of formula IX can be prepared by reacting an acid of the formula $X^1$—C(H,OH)—COOH with an amine of the formula IV.

Preferred compounds of formulas I and V-1 are those in which the substituent R$^{11}$ present in a phenyl group Z is hydroxy, lower-alkanoyloxy, sulfamoyl or a group R$^1$, —O—(CH$_2$)$_q$—OH or —O—(CH$_2$)$_q$—O—(CH$_2$)$_r$—R$^5$ and R$^5$ is hydrogen, lower-alkyl or phenyl.

Further preferred compounds are those compounds of formulas I and V-1 in which R is hydrogen; those in which $X^1$ is phenoxymethyl and $X^2$ is phenoxymethyl or phenyl, especially those in which the C-atom bonded to a phenoxymethyl residue $X^1$ or $X^2$ has the S-configuration or the C-atom bonded to a phenyl residue has the R-configuration.

Furthermore, those compounds of formulas I and V-1 in which Y is methyl, especially those in which the C-atom bonded to a methyl residue Y has the R-configuration, are preferred.

Furthermore, those compounds of formula I and V-1 in which Z is phenyl or thienyl substituted by carbamoyl, methoxycarbonyl or 2-(ethoxy or methoxy)-carbonyl-1-methylvinyl, are preferred.

Furthermore, those compounds of formulas I and V-1 in which Z is phenyl substituted by 6-hydroxyhexoxy, 2-phenethoxy-2-ethoxy or (ethoxy or methoxy)-carbonylmethoxy, are preferred.

Furthermore, those compounds of formula V-1 in which Z is p-hydroxyphenyl, are preferred.

Especially preferred compounds of formulas I and V-1 are those in which R is hydrogen, $X^1$ is phenoxymethyl, $X^2$ is phenoxymethyl or phenyl, Y is methyl and Z is phenyl or thienyl substituted by carbamoyl, methoxycarbonyl or 2-(ethoxy or methoxy)-carbonyl-1-methylvinyl, or phenyl substituted by 6-hydroxyhexoxy, 2-phenethoxy-2-ethoxy or (ethoxy or methoxy)-carbonylmethoxy.

Further, especially preferred compounds of formula V-1 are those in which R is hydrogen, $X^1$ is phenoxymethyl, Y is methyl and Z is p-hydroxyphenyl.

Furthermore, especially preferred compounds of formulas I and V-1 are those in which the C-atom bonded to a methyl residue Y has the R-configuration, the C-atom bonded to a phenoxymethyl residue $X^1$ or $X^2$ has the S-configuration and the C-atom bonded to a phenyl residue $X^2$ has the R-configuration.

Examples of preferred compounds of formula I are:
1,1′-[[(R)-α-methyl p-[2-(phenethoxy)ethoxy]phenethyl]imino]bis[(S) -3-phenoxy-2-propanol],
methyl (E)-p-[(R)-2-[bis[(RS) -2-hydroxy-3-phenoxypropyl]amino]propyl]-β-methyl-cinnamate,
methyl p-[(R)-2-[bis[(RS) -2-hydroxy-3-phenoxypropyl]amino]propyl]benzoate and
6-[p-[(R)-[bis[(S)-hydroxy -3-phenoxypropyl]amino]propyl]phenoxy-1-hexanol.

Examples of preferred compounds of formula V-1 are:
(S)-1-[[(R)-α-methyl-p-[2 -(ethoxy)ethoxy]phenethyl]amino]-3-phenoxypropanol,
methyl 2-[p-[2-[[(RS) -2-hydroxy-3-phenoxypropyl]amino]propyl]phenoxy]acetate,
methyl (E)-p-[(R)-2-[[(RS) -2-hydroxy-3-phenoxypropyl]amino]propyl]-β-methyl-cinnamate,
p-[(R)-3-[[(RS)-2-hydroxy -3-phenoxypropyl]amino]butyl]benzamide,
methyl p-[(R)-2-[bis[(RS) -2-hydroxy-3-phenoxypropyl]amino]propyl]benzoate,
p-[(R)-2-[[(S)-2-hydroxy -3-phenoxypropyl]amino]propyl]phenol and
6-[p-[(R)-2-[[(S)-2-hydroxy -3-phenoxypropyl]amino]propyl]phenoxy]hexanol.

The amines of formulas I and V-1 as well as the physiologically compatible salts thereof can be used as active ingredients in pharmaceutical preparations for the treatment of obesity and/or of diabetes mellitus, especially of obese adult diabetics. In an animal experiment an increased catabolism, primarily of fat, has been observed upon the administration of the above compounds. Furthermore, it has been observed that the compounds stimulate the formation of brown adipose tissue in rats and obesehyperglycemic mice. It is known that defects of the brown adipose tissue play a substantial role in the origin of obesity. In obese-hyperglycemic mice the compounds have a pronounced antidiabetic effect, in that they have hypoglycemic activity and reduce glycosuria. These compounds exhibit only a slight activity on the working of the heart and circulation. The dosage which can be administered is in the range of 0.5–1000 mg, preferably 2–200 mg, per day, for an adult depending on the activity of the individual compounds and on the individual requirements of the patients or warm-blooded host, whereby the dosage can be administered as a single dose or in several divided doses over the day.

In addition, in an animal experiment with the above compounds an increase in the body protein content and a decrease in the fat content can be detected. These compounds therefore lead to an increase in the lean composition of the body at the expense of fat. Accordingly, they can be used above all in human medicine for the treatment of conditions which are associated with high protein breakdown, for example, in convalescence after an operation. In this case the dosages administered lie in the same range as in the treatment of obesity and/or of diabetes mellitus.

The above compounds can also be used in the maintenance of fattening animals such as beef cattle, pigs, sheep and poultry. In this case the dosage forms administered can be the same as in the case of vitamins. These compounds can also be used as feed additives in dosages of 0.01–100 mg/kg depending on the substance, kind of animal and age.

The pharmaceutical preparations contain the active substance together with a compatible pharmaceutical-organic or inorganic carrier material such as, for example, water, gelatine, gum arabic, lactose, starch, magnesium stearate, talc, vegetable oils, polyalkylene glycols, and the like. The pharmaceutical preparations are preferably administered orally, for example, in the form of tablets, capsules, pills, powders, granulates, solutions, syrups, suspensions or elixirs. The administration can, however, also be carried out parenterally, for example, in the form of sterile solutions, suspensions or emulsions. The pharmaceutical preparations can be sterilized and/or can contain ingredients such as preserving agents, stabilizers, wetting agents, emulsifiers, salts for varying the osmotic pressure and buffer substances.

The activity of the above compounds is evident from the following test results:

1) Activity on Oxygen Consumption

Male albino rats weighing 160–180 g were placed in metabolic cages after fasting for 24 hours. The cages were ventilated with a constant 6 liters room air/minute which was equilibrated at a dew point of 11° C. Samples of the spent air were collected during periods of in each case 14 minutes after again equilibrating and the oxygen content and carbon dioxide content were analyzed. After an adaptation time of 4 hours, the animals, divided into groups of 6, received either placebo (5% gum arabic) or the test substance (suspended in 5% gum arabic) per os. Thereafter, the determinations were carried out for a period of 12 hours. In Table I there is given the percentage of the average oxygen consumption after medication during the first 3 hours and the entire test duration (12 hours) of the oxygen consumption of the adaptation period, corresponding corrections for variations in the placebo group having been taken into consideration.

TABLE I

| Compound prepared in the Example No. | Dosage μM/kg | $O_2$ (oxygen) consumption of the % of the value of pre-period | |
|---|---|---|---|
| | | 1st–3rd hour | 1st–12th hour |
| 1 | 10 | 133 | 125 |
| 2 | 10 | 122 | 114 |
| 3 | 10 | 132 | 110 |
| 4 | 10 | 121 | 111 |
| 5 | 100 | 151 | 118 |
| 6 | 10 | 113 | 110 |
| 7 | 30 | 144 | 121 |
| 9 | 10 | 138 | 110 |
| 10a) | 30 | 143 | 114 |
| 10b) | 3 | 126 | 107 |
| 10c) | 3 | 130 | 110 |
| 10d) | 10 | 132 | 110 |
| 10e) | 10 | 176 | 149 |
| 10f) | 30 | 150 | 112 |
| 10g) | 10 | 126 | 112 |
| 11 | 3 | 127 | 112 |
| 12a) | 10 | 145 | 130 |
| 12b) | 10 | 148 | 137 |
| 13a) | 30 | 123 | 115 |
| 13b) | 30 | 136 | 113 |
| 14a) | 3 | 134 | 110 |
| 14b) | 10 | 121 | 111 |
| 15a) | 3 | 140 | 118 |
| 16a) | 10 | 136 | 113 |
| 16b) | 100 | 145 | 120 |
| 17a) | 1 | 139 | 118 |
| 17b) | 3 | 136 | 120 |
| 18a) | 1 | 155 | 130 |
| 18b) | 3 | 135 | 120 |
| 19a) | 30 | 139 | 111 |
| 19b) | 100 | 123 | 107 |
| 20a) | 3 | 164 | 141 |
| 20b) | 3 | 146 | 129 |
| 21a) | 10 | 150 | 121 |
| 21b) | 30 | 136 | 122 |
| 22 | 30 | 156 | 124 |
| 32a) | 1 | 131 | 120 |
| 36b) | 10 | 165 | 136 |
| 37 | 3 | 156 | 122 |
| 38 | 30 | 173 | 146 |
| 41 | 1 | 170 | 124 |
| 42 | 3 | 166 | 127 |

2) Catabolic Activity on Lipids

Groups of 4 male albino rats weighing 320–360 g were kept in metabolic cages without access to feed. Oxygen consumption and Carbon dioxide production were measured during 12 hours. After 4 hours, the animals received placebo (5% gum arabic) or the test substance (suspended in gum arabic) per os. In Table II there is given the average decrease of the respiratory quotient ($CO_2/O_2$) during 8 hours after administration of the test substance in comparison to the last 3 hours before administration of the test substance. Variations appearing in the placebo group were taken into consideration in the calculation.

TABLE II

| Compound prepared in Example No. | Dosage μM/kg | Variation of the respiratory quotient |
|---|---|---|
| 10b) | 10 | −0.037 |
| 10e) | 10 | −0.041 |

TABLE II-continued

| Compound prepared in Example No. | Dosage μM/kg | Variation of the respiratory quotient |
|---|---|---|
| 14a) | 30 | −0.072 |
| 17a) | 3 | −0.038 |

3) Activity on Urine Glucose and Blood Glucose and the Formation of Brown Adipose Tissue Female hyperglycemic fat mice were adapted to an amount of feed limited to 3 g/day/animal. The test compounds (suspended in 5% gum arabic) or placebo (5% gum arabic) were administered orally twice daily during a period of 15 days. Urine was collected for 6 days a week and urine glucose was determined. Blood glucose and the weight of the interscapular brown adipose tissue were determined at the end of the test.

The test results are given in Table III as a percentage of the control value.

TABLE III

| Compound prepared in Example No. | Dosage μM/kg per day | Urine glucose 1st week/2nd week | | Blood glucose | Brown adipose tissue |
|---|---|---|---|---|---|
| 14a) | 60 | 89% | 31% | 54% | 237% |
| 17b) | 60 | 5% | 5% | 46% | 184% |

The starting materials used in the following Examples, especially the amines of formula V in which $X^4$ is lower-alkyl or phenyl optionally monosubstituted by fluorine, chlorine, trifluoromethyl or lower-alkoxy and the amines of formula IV, are known or can be prepared in a known manner, for example, as described hereinafter or in European Patent Applications 6735, 21636 and 94595.

For the preparation of the amine starting materials of Examples 1 and 10e (RS)-4-(2-thienyl)-2-butanol, acetyl chloride and aluminum chloride were reacted in methylene chloride to give (RS)-3-(5-acetyl-2-thienyl)-1-methylpropyl acetate. This was saponified with sodium hydroxide in methanol to give (RS)-5-(3-hydroxybutyl)-2-thienyl methyl ketone. The resulting ketone reacted with triethyl phosphonoacetate in ethanol in the presence of sodium ethanolate to give ethyl (E)-5-[(RS)-3-hydroxybutyl]-β-methyl-2-thiopheneacrylate. Reaction with p-toluenesulfonyl chloride and subsequent treatment with sodium azide gave ethyl (E)-5-[(RS)-3-azidobutyl]-β-methyl-2-thiopheneacrylate. Therefrom there was obtained by reduction with triphenylphosphine and subsequent hydrolysis ethyl (E)-5-[(RS)-3-aminobutyl]-β-methyl-2-thiopheneacrylate, $\epsilon_{320}=17465$.

For the preparation of the amine starting material of Example 5,2-(2-thienyl)ethyl-p-toluenesulfonate, acetyl chloride and aluminum chloride were reacted in methylene chloride to give 2-[(5-acetyl-2-thienyl)ethyl]-p-toluenesulfonate (m.p. 111°-112°, from ethanol). The latter was converted with sodium azide in dimethyl sulfoxide into 5-(2-azidoethyl)-2-thienyl methyl ketone. Oxidation with sodium hypobromite yielded 5-(2-azidoethyl)-2-thiophenecarboxylic acid of m.p. 53°-55°, which with thionyl chloride gave the corresponding acid chloride, which was reacted with ammonia to give 5-(2-azidoethyl)-2-thiophenecarboxamide (m.p. 104°-105° from ethanol). Reaction with triphenylphosphine and hydrolysis gave 5-(2-aminoethyl)-2-thiophenecarboxamide, m.p. 134°-136° (from acetonitrile).

For the preparation of the amine starting material of Examples 6 and 10g, 5-[(RS)-2-hydroxypropyl]-2-thienyl methyl ketone and triethyl phosphonoacetate were reacted in ethanol in the presence of sodium ethylate to give ethyl (E)-5-[(RS)-2-hydroxypropyl]-β-methyl-2-thiopheneacrylate. With p-toluenesulfonyl chloride, there was obtained therefrom ethyl (E)-β-methyl-5-[(RS)-2-[(p-toluenesulphonyl)oxy]propyl]-2-thiopheneacrylate (m.p. 121°, from methylene chloride-alcohol. Reaction with sodium azide in dimethylsulfoxide gave ethyl (E)-5-[(RS)--2-azido-propyl]-β-methyl-2-thiopheneacrylate. Reduction with triphenylphosphine and hydrolysis yielded ethyl (E)-5-[(RS)-2-aminopropyl]-β-methyl-2-thiopheneacrylate, $\epsilon_{320}=17970$.

For the preparation of the amine starting material of Example 7,4-(5-acetyl-2-thienyl)-2-butanone was reacted with ethylene glycol, triethyl o-formate and p-toluenesulfonic acid in methylene chloride selectively to give methyl 5-[2-(2-methyl-1,3-dioxolan-2-yl)ethyl]-2-thienyl ketone. Oxidation with sodium hypobromite and subsequent hydrolysis gave 5-(3-oxobutyl)-2-thiophenecarboxylic acid. With sodiumborohydride there was obtained therefrom 5-(3-hydroxy-butyl)-2-thiophenecarboxylic acid which was converted in dimethylacetamide with methyl iodide and sodium bicarbonate into the methyl ester. Treatment with p-toluene-sulfonyl chloride in pyridine and reaction with sodium azide in dimethylsulfoxide gave methyl 5-(3-azidobutyl)-2-thiophenecarboxylate from which the corresponding acid was obtained by saponification. With thionyl chloride there was prepared its acid chloride from which, with concentrated ammonia in diethyl ether, there was obtained 5-(3-azidobutyl)-2-thiophenecarboxamide. Reduction of the azido group with triphenylphosphine and subsequent hydrolysis gave (R,S)-5-(3-aminobutyl)-2-thiophenecarboxamide, m.p. 65°-75°, $\epsilon_{256}=7780$, $\epsilon_{275}=9900$.

For the preparation of the amine starting material of Example 8, (RS)-5-(3-hydroxybutyl)-2-thienyl methyl ketone is reacted with p-toluenesulfonyl chloride to give (RS)-3-(5-acetyl-2-thienyl)-1-methylpropyl-p-toluenesulfonate, m.p. 61°-63°. With sodium azide there is obtained therefrom methyl (RS)-5-(3-azidobutyl)-2-thienyl ketone which is catalytically hydrogenated to give 2-acetyl-5-[(RS)-3-aminobutyl]thiophene.

For the preparation of the amine starting material of Example 9 2-(p-toluenesulfonyloxy)-propylthiophene was reacted with acetyl chloride and aluminum trichloride in methylene chloride to give 5-acetyl-2-(p-toluenesulfonyloxy)-propylthiophene. With sodium azide in dimethylsulfoxde there was obtained therefrom 5-(3-azidopropyl)-2-thienyl methyl ketone. Oxidation with sodium hypobromite gave 5-(3-azidopropyl)-2-thiophenecarboxylic acid, m.p. 71°-72°. Reaction of the resulting acid with thionyl chloride and subsequent treatment with concentrated ammonia yielded 5-(3-azidopropyl)-2-thio-phenecarboxamide, m.p. 85°-87°. There was obtained from the foregoing reaction mixture, after treatment with triphenylphosphine and hydrolysis, 5-(3-aminopropyl)-2-thiophenecarboxamide, m.p. 143.5°-144° (from water).

For the preparation of the starting material of Example 10a, p-(2-bromoethyl)-acetophenone was reacted with sodium azide in dimethylsulfoxide to give p-(2-azidoethyl)acetophenone. Oxidation with sodium hypobromite gave p-(2-azidoethyl)benzoic acid (m.p. 130°-131°, from acetone-hexane), which was converted with thionyl chloride into the corresponding acid chloride and subsequently with ammonia into p-(2-azidoethyl)benzamide. Treatment with triphenylphosphine and hydrolysis gave p-(2-aminoethyl)benzamide, m.p. 132°-133° (from ethanol).

For the preparation of the amine starting material of Example 10b, methyl 5-(3-aminopropyl)-2-thiophenecarboxylate, 5-(3-azidopropyl)-2-thiophenecarboxylic acid is esterified with methyl iodide and the thus-obtained methyl 5-(3-azidopropyl)-2-thiophenecarboxylate is catalytically hydrogenated.

For the preparation of the amine starting material of Example 10f, α-methyl-2-thiophenethanol, acetyl chloride and aluminum chloride were reacted in methylene chloride to give (RS)-2-(5-acetyl-2-thienyl)-1-methylethyl acetate. The resulting acetate was saponified with sodium hydroxide in methanol to give 5-[(RS)-2-hydroxypropyl]-2-thienyl methyl ketone which was subsequently reacted with p-toluenesulfonyl chloride to give (RS)-2-(5-acetyl-2-thienyl)-1-methylethyl-p-toluenesulfonate, m.p. 101°-103°. With sodium azide in dimethylsulfoxide there was obtained therefrom 5-[(RS)-2-azidopropyl]-2-thienyl methyl ketone which was oxidized with bromine in sodium hydroxide solution to give 5-[(RS)-2-azidopropyl]-2-thiophenecarboxylic acid. With thionyl chloride, there was obtained therefrom the corresponding acid chloride and from this there was prepared with ammonia 5-[(RS)-2-azidopropyl]-2-thiophenecarboxamide, m.p. 79°-80° C., from diethyl ether. Treatment with triphenylphosphine and hydrolysis gave 5-[(RS)-2-aminopropyl]-2-thiophenecarboxamide, m.p. 91°-92° from acetonitrile.

For the preparation of the amine starting material of Example 24, p-aminosulfonylbenzaldehyde was reacted with diethyl cyanomethylphosphonate/sodium hydride in tetrahydrofuran to give 1-cyano-2-(4-aminosulfonylphenyl)-ethane which was hydrogenated in methanol with Raney-cobalt as the catalyst to give 3-(4-aminosulfonylphenyl)-propylamine.

The Examples which follow further illustrate the invention.

EXAMPLE 1

2 g of ethyl (E)-5-[(RS)-3[[(R)-2-hydroxyphenethyl]-amino]butyl]-β-methyl-2-thiopheneacrylate (m.p. 72°) and 850 mg of phenyl glycidyl ether were heated to 90° in 20 ml of dimethylsulfoxide. Additional 850 mg of phenyl glycidyl ether were added after 20 hours and the mixture was heated to 90° for an additional 20 hours. After cooling, the reaction mixture was poured into water and extracted with methylene chloride. Chromatography of the crude product gave 1.8 g of ethyl (E)-5-[(RS)-3-[[(R)-2-hydroxy-phenethyl]-[(RS)-2-hydroxy-3-phenoxypropyl]amino]butyl]-β-methyl-2-thiopheneacrylate, $[\alpha]_D = -27°$ (0.1% in methanol), $\epsilon_{323} = 16170$.

EXAMPLE 2

In a manner analogous to Example 1, from 1.6 g of 5-[(RS)-3-[[(S)-β-hydroxy-m-(trifluoromethyl)phenethyl]-amino]butyl]-2-thiophenecarboxamide (m.p. 165°-166°) and 1.25 g of phenyl glycidyl ether, there were prepared 800 mg of 5-[(RS)-3-[[(RS)-2-hydroxy-3-phenoxypropyl]-[(RS)-2-hydroxy-m-(trifluoromethyl)-phenethyl]amino]butyl]-2-thiophenecarboxamide, $\epsilon_{271} = \epsilon_{276} = 12210$.

EXAMPLE 3

5-[(RS)-3-[[(R)-2-Hydroxyphenethyl]-[(RS)-2-hydroxy-3-phenoxypropyl]amino]butyl]-2-thiophenecarboxamide, $[\alpha]_D = -25°$ (0.1% in methanol), $\epsilon_{276} = 11780$, was prepared in analogy to Example 1.

EXAMPLE 4

5-[(RS)-3-[[(R)-β-Hydroxyphenethyl]-[(RS)-2-hydroxy-3-phenoxypropyl]amino]butyl]-2-thienyl methyl ketone, $[\alpha]_D = -10°$ (0.1% in methanol), $\epsilon_{296} = 11930$, was prepared in analogy to Example 1.

EXAMPLE 5

3.4 g of 5-(2-aminoethyl)-2-thiophenecarboxamide and 2.7 ml of 2,3-epoxypropyl phenyl ether were heated to 90° in 30 ml of dimethylsulfoxide for 18 hours. The reaction mixture was poured into water and extracted with methylene chloride. The dried methylene chloride solutions were evaporated and the residue was chromatographed on silica gel with ether-methanol. There were obtained 1.5 g of 5-[2-[bis-[(RS)-2-hydroxy-3-phenoxypropyl]amino]ethyl]-2-thiophenecarboxamide, $\epsilon_{277} = 12580$.

EXAMPLE 6

In analogy to Example 5, from ethyl (E)-5-[(RS)-2-aminopropyl]-β-methyl-2-thiopheneacrylate and 2,3-epoxypropyl phenyl ether, there was obtained ethyl (E)-5-[(RS)-2-[bis-[(RS)-2-hydroxy-3-phenoxypropyl]amino]propyl]-β-methyl-2-thiopheneacrylate, $\epsilon_{324} = 17260$.

EXAMPLE 7

In analogy to Example 5, from 2,3-epoxypropyl phenyl ether and (RS)-5-(3-aminobutyl)-2-thiophenecarboxamide, there was prepared 5-[(RS)-3-[bis-[(RS)-2-hydroxy-3-phenoxypropyl]amino]butyl]-2-thiophenecarboxamide, $\epsilon_{270} = 12740$, $\epsilon_{276} = 13090$.

EXAMPLE 8

In analogy to Example 5, from 2,3-epoxypropyl phenyl ether and 2-acetyl-5-[(RS)-3-aminobutyl]thiophene, there was prepared 5-[(RS)-3-[bis-[(RS)-2-hydroxy-3-phenoxypropyl]amino]butyl]-2-thienyl methyl ketone, $\epsilon_{270} = 10770$, $\epsilon_{277} = 10220$, $\epsilon_{296} = 11860$.

EXAMPLE 9

921 mg of 5-(3-aminopropyl)-2-thiophenecarboxamide and 0.68 ml of 2,3-epoxypropyl phenyl ether were heated to 90° in 15 ml of dimethylsulfoxide for 14 hours. The reaction mixture was poured into water and extracted with methylene chloride. The dried methylene chloride solutions were evaporated in vacuo and the residue was chromatographed on silica gel, whereby there were obtained 800 mg of 5-[3-[[(RS)-2-hydroxy-3-phenoxypropyl]amino]propyl]-2-thiophenecarboxamide, m.p. 129°-130°, $\epsilon_{276} = 12130$.

EXAMPLE 10

In analogy to Example 9, there were prepared:
a) p-[2[[(RS)-2-Hydroxy-3-phenoxypropyl]amino]ethyl]benzamide, m.p. 133°-135°, $\epsilon_{222} = 16200$;
b) methyl 5-[3-[[(RS)-2-hydroxy-3-phenoxypropyl]amino]propyl]-2-thiophenecarboxylate, m.p. 90°-91°, $\epsilon_{277} = 13510$;

c) 5-[(RS)-3-[[(RS)-2-hydroxy-3-phenoxypropyl]amino]butyl]-2-thiophenecarboxamide, m.p. 126°–128°, $\epsilon_{276} = 12310$;

d) 5-[2-[[(RS)-2-hydroxy-3-phenoxypropyl]amino]ethyl]2-thiophenecarboxamide, m.p. 115°–117°, $\epsilon_{276} = 11930$;

e) ethyl (E)-5-[(RS)-3-[[(RS)-2-hydroxy-3-phenoxypropyl]amino]butyl]-β-methyl-2-thiopheneacrylate, $\epsilon_{321} = 17130$;

f) 5-[(RS)-2-[[(RS)-2-hydroxy-3-phenoxypropyl]amino]propyl]-2-thiophenecarboxamide, $\epsilon_{277} = 11370$;

g) ethyl (E)-5-[(RS)-2-[[(RS)-2-hydroxy-3-phenoxypropyl]amino]propyl]-β-methyl-2-thiopheneacrylate, $\epsilon_{320} = 17390$;

h) 5-[(RS)-3-[[(RS)-2-hydroxy-3-phenoxypropyl]amino]butyl]-2-thienyl methyl ketone, $\epsilon_{264} = 9850$, $\epsilon_{294} = 12100$.

EXAMPLE 11

A mixture of 1.02 g of p-[(R)-3-[[(RS)-2-hydroxy-3-phenoxypropyl]amino]butyl]benzamide and 1.8 g of R-styrene oxide in 30 ml of dimethylsulfoxide was heated to 100° for 70 hours. The reaction solution was evaporated in a high vacuum and the residue was chromatographed on silica gel. 0.8 g of pure, amorphous p-[(R)-3-[[(R)-β-hydroxyphenethyl][(RS)-2-hydroxy-3-phenoxypropyl]amino]butyl]benzamide, $[\alpha]_D^{20} = -60°$ (c=0.6 in methanol), $\epsilon_{220} = 18190$, $\epsilon_{234} = 13765$, was eluted with chloroform/n-propanol/25% NH3 (230:20:2).

EXAMPLE 12

In analogy to Example 11, there were prepared as amorphous products:
a) Methyl p-[(R)-2-[[(R)-β-hydroxyphenethyl][(RS)-2-hydroxy-3-phenoxypropyl]amino]propyl]benzoate, $[\alpha]_D^{20} = -68°$ (c=0.5 in methanol), $\epsilon_{220} = 17030$, $\epsilon_{237} = 13680$; and b) methyl p-[(R)-2-[[(R)-β-hydroxyphenethyl][(RS)-2-hydroxy-3-phenoxypropyl]amino]propyl]-β-methyl-cinnamate, $[\alpha]_D^{20} = -63°$ (c=0.5 in methanol), $\epsilon_{270} = 17310$, $\epsilon_{277} = 17900$.

EXAMPLE 13

A mixture of 3.8 g of S-1-methyl-3-(4-aminocarbonylphenyl)propylamine and 3.60 g of 2,3-epoxypropyl phenyl ether in 30 ml of ethanol and 20 ml of acetonitrile was heated under reflux for 8 hours. The reaction solution was then evaporated in vacuo and the residue was chromatographed on 250 g of silica gel. 2.4 g of amorphous p-[(S)-3-bis-[[(RS)-2-hydroxyphenoxypropyl]amino]butyl]benzamide, $[\alpha]_D^{20} = +29°$ (c=0.4 in methanol), $\epsilon_{220} = 24025$, $\epsilon_{237} = 12940$, were first eluted with the mixture chloroform/n-propanol/25% ammonia (1000:50:5).

3.5 g of pure p-[(S)-3-[[(RS)-2-hydroxy-3-phenoxypropyl]amino]butyl]benzamide, m.p. 133°–136° (from acetonitrile), $[\alpha]_D^{20} = -2°$ (c=0.8 in methanol), $\epsilon_{223} = 15510$, $\epsilon_{236} = 13820$, were subsequently eluted with the mixture chloroform/n-propanol/25% ammonia (100:10:1).

EXAMPLE 14

In analogy to Example 13, there were prepared using R-1-methyl-3-(4-aminocarbonylphenyl)propylamine:
a) p-[(R)-3-[[(RS)-2-Hydroxy-3-phenoxypropyl]amino]butyl]benzamide, m.p. 132°–136° (acetonitrile), $[\alpha]_D^{20} = +2°$ (c=1.0 in methanol), $\epsilon_{222} = 15250$, $\epsilon_{236} = 13630$; and b) p-[(RS)-2-bis[[(RS)-2-hydroxy-3-phenoxypropyl]amino]butyl]benzamide, amorphous, $[\alpha]_D^{20} = -29°$ (c=0.4 in methanol), $\epsilon_{220} = 23700$, $\epsilon_{236} = 13010$.

EXAMPLE 15

In analogy to Example 13, there were prepared using (S)-2,3-epoxypropyl phenyl ether and R-1-methyl-3-(4-aminocarbonylphenyl)propylamine
a) p-[(R)-3-[[(S)-2-hydroxy-3-phenoxypropyl]amino]butyl]benzamide, m.p. 129°–130° (ethanol), $[\alpha]_D^{20} = +3°$ (c=1.0 in methanol), $\epsilon_{233} = 14990$, $\epsilon_{236} = 13290$; and b) p-[(R)-3-bis[[(S)-2-hydroxy-3-phenoxypropyl]amino]butyl]benzamide, $[\alpha]_D^{20} = -24°$ (c=0.56 in methanol, $\epsilon_{221} = 22510$, $\epsilon_{237}12650$.

EXAMPLE 16

In analogy to Example 13, there were prepared:
a) (RS)-p-[3-[(2-hydroxy-3-phenoxypropyl)amino]propyl]benzamide. m.p. 121°–122° (acetone), $\epsilon_{222} = 15170$, $\epsilon_{235} = 13540$; and b) (RS)-p-[3-bis[(2-hydroxy-3-phenoxypropyl)amino]propyl]-benzamide, amorphous, $\epsilon_{220} = 25010$, $\epsilon_{236} = 13930$.

EXAMPLE 17

In analogy to Example 13, there were prepared using methyl p-[(R)-2-aminopropyl]-β-methyl-cinnamate:
a) Methyl (E)-p-[(R)-2-[[(RS)-2-hydroxy-3-phenoxypropyl]amino]propyl]-β-methyl-cinnamate, m.p. 70°–72° (acetone-hexane), $[\alpha]_D^{20} = -22°$ (c=0.7 in methanol), $\epsilon_{271} = 19960$, $\epsilon_{276} = 20030$; and b) methyl (E)-p-[(R)-2-[bis[(RS)-2-hydroxy-3-phenoxypropyl]amino]propyl]-β-methyl-cinnamate, amorphous, $[\alpha]_D^{20} = -37°$ (c=0.27 in methanol), $\epsilon_{271} = 15570$, $\epsilon_{277} = 19910$.

EXAMPLE 18

In analogy to Example 13, there were prepared using (S)-2,3-epoxypropyl phenyl ether and methyl p-[(R)-2-aminopropyl]-β-methyl-cinnamate:
a) Methyl p-[(R)-2-[[(S)-2-hydroxy-3-phenoxypropyl]amino]propyl]-β-methyl-cinnamate, m.p. 63°–64° (ether-hexane), $[\alpha]_D^{20} = -25°$ (c=0.9 in methanol): $\epsilon_{220} = 19950$, $\epsilon_{272} = 19125$, $\epsilon_{277} = 19125$; and b) methyl p-[(R)-2-[bis[(S)-2-hydroxy-3-phenoxypropyl]amino]propyl]-β-methyl-cinnamate, amorphous, $[\alpha]_D^{20} = -9.4°$ (c=0.8 in methanol), $\epsilon_{220} = 27200$, $\epsilon_{271} = 17700$, $\epsilon_{277} = 18000$.

EXAMPLE 19

In analogy to Example 13, there were prepared using (S)-2,3-epoxypropyl phenyl ether and p-[(R)-2-aminopropyl]acetophenone:
a) 4'-[(R)-2-[[(S)-2-Hydroxy-3-phenoxypropyl]amino]propyl]acetophenone, m.p. 72°–78° (acetonitrile), $[\alpha]_D^{20} = -26°$ (c=1.0 in methanol), $\epsilon_{253} = 15280$, $\epsilon_{276} = 4700$; and b) 4'-[(R)-2-[bis[(S)-2-hydroxy-3-phenoxypropyl]amino]propyl]acetophenone, amorphous, $[\alpha]_D^{20} = -24°$ (c=1.0 in methanol), $\epsilon_{256} = 11780$, $\epsilon_{270} = 9570$, $\epsilon_{277} = 7650$.

EXAMPLE 20

In analogy to Example 13, there were prepared using 2,3-epoxypropyl phenyl ether and methyl p-[(R)-2-aminopropyl]benzoate:

a) Methyl p-[(R)-2-[[(RS)-2-hydroxy-3-phenoxypropyl]amino]propyl]benzoate, amorphous, $[\alpha]_D^{20} = -23°$ (c=0.9 in methanol), $\epsilon_{222} = 13890$, $\epsilon_{238} = 14890$; and b) methyl p-[(R)-2-[bis[(RS)-2-hydroxy-3-phenoxypropyl]amino]propyl]benzoate, amorphous, $[\alpha]_D^{20} = -35°$ (c=1.0 in methanol), $\epsilon_{220} = 23480$, $\epsilon_{238} = 13190$.

EXAMPLE 21

In anology to Example 13, there were prepared using 2,3-epoxypropyl 2'-fluorophenyl ether and R-1-methyl3-(4-aminocarbonylphenyl)propylamine:

a) p-[(R) -3-[[(RS)-(o-Fluorophenoxy)-2-hydroxypropyl]-amino]butyl]benzamide, m.p. 114°–116° (acetonitrile, $[\alpha]_D^{20} = +2.4°$ (c=1.0 in methanol), $\epsilon_{220} = 14145$, $\epsilon_{236} = 13720$; and b) p-[(R)-3-[bis[(RS)-(o-fluorophenoxy)-2-hydroxypropyl]amino]butyl]benzamide, amorphous, $[\alpha]_D^{20} = -33°$ (c=0.6 in methanol), $\epsilon_{220} = 21670$, $\epsilon_{236} = 12860$.

EXAMPLE 22

In analogy to Example 13, there was prepared using 2,3-epoxypropyl 2'-chlorophenyl ether and methyl p-[(R)2-aminopropyl]-β-methyl-cinnamate:

Methyl p-[(R)-2-[[(RS)-3-(o-chlorophenoxy)-2-hydroxypropyl]amino]propyl]-β-methyl-cinnamate, amorphous, $[\alpha]_D^{20} = -19°$ (c=1.0 in methanol), $\epsilon_{218} = 19865$, $\epsilon_{274} = 19865$, $\epsilon_{281} = 18910$.

EXAMPLE 23

A mixture of 4.0 g of tyramine and 5.25 g of phenyl glycidyl ether in 100 ml of dimethylsulfoxide was heated to 100° for 17 hours. The solvent was evaporated in vacuo and the residue was chromatographed on 400 g of silica gel. 4.3 g of p-[2-[bis[(RS)-2-hydroxy-3-phenoxypropyl]amino]ethyl]phenol was firstly eluted with chloroform/npropanol/concentrated ammonia (1000:10:1) as an amorphous substance, $\epsilon_{218} = 20710$. The further fractions yielded 4.2 g of pure (RS)-p-[2-[(2-hydroxy-3-phenoxypropyl) amino]ethyl]phenol of m.p. 122°–124°, $\epsilon_{221} = 15310$.

EXAMPLE 24

In analogy to Example 23, there were prepared using 3-(4-aminosulfonylphenyl)propylamine and phenyl glycidyl ether:

(RS)-p-[3-[(2-Hydroxy-3-phenoxypropyl)amino]-propyl]benzenesulfonamide, m.p. 119°–120° (from acetonitrile), $\epsilon_{221} = 20160$; and p-[2-[bis[(RS)-2-hydroxy-3-phenoxypropyl]amino]-propyl]benzenesulfonamide, amorphous, $\epsilon_{222} = 27450$.

EXAMPLE 25

Methyl p-[(R)-2-[[(RS)-3-phenoxy-2-hydroxypropyl]amino]propyl]-5-phenyl-3,5-dimethylpenta-2,4-dienoate, amorphous, $[\alpha]_D^{20} = -20°$ (c=0.5 in methanol), $\epsilon_{270} = 11860$, $\epsilon_{276} = 12850$, $\epsilon_{294} = 13610$, was prepared in analogy to Example 23 using phenyl glycidyl ether and methyl p-[(R)-2-aminopropyl]-5-phenyl-3,5-dimethyl-penta-2,4-dienoate.

EXAMPLE 26

Methyl p-[(R)-2-[[(RS)-3-phenoxy-2-hydroxypropyl]amino]propyl]-4-phenyl4-oxobutyrate, amorphous, $[\alpha]_D^{20} = -20°$ (c=0.3 in methanol), $\epsilon_{251} = 15250$, was prepared in analogy to Example 23 using phenyl glycidyl ether and methyl p-[(R)-2-aminopropyl]-4-phenyl-4-oxobutyrate.

EXAMPLE 27

A solution of 342 mg of p-[(R)-3-[[(RS)-2-hydroxy-3-phenoxypropyl]amino]-butyl]benzamide in 5 ml of methanol was treated with 44 mg of hydrochloric acid gas in 1 ml of methanol. The solution was concentrated to 3 ml and treated with 3 ml of ether. After standing at 0° for several hours, the separated crystals were removed by filtration under suction and recrystallized from methanolether. The p-[(R)-3-[[(RS)-2-hydroxy-3-phenoxypropyl]amino]butyl]-benzamide hydrochloride obtained melted at 156°–158°, $[\alpha]_D^{20} = +12°$ (c=0.7 in methanol), $\epsilon_{234} = 13410$, $\epsilon_{222} = 14970$.

The oxalate was prepared analogously with oxalic acid, m.p. 199°–200°, $[\alpha]_D^{20} + +8°$ (c=0.8 in methanol), $\epsilon_{222} = 15920$, $\epsilon_{235} = 13680$.

EXAMPLE 28

A mixture of 1.0 g of p-[(R)-3-[[(RS)-2-hydroxy-3-phenoxypropyl]amino]butyl]benzamide, 500 mg of lithium aluminum hydride and 100 ml of absolute tetrahydrofuran was heated under reflux for 2 hours. The mixture was treated cautiously with 20 ml of warm ether and subsequently with 2 ml of sodium sulfate. The separated precipitate was removed by filtration and the filtrate was evaporated in vacuo. The residue was dissolved in 6 ml of methanol and treated with 250 mg of oxalic acid. 25 ml of ether were then added to the clear solution and the mixture was left to crystallize out in a refrigerator, and there was obtained 0.8 g of p-[(R)-3-[[(RS)-2-hydroxy-3-phenoxypropyl]amino]butyl]benzylamine oxalate of m.p. 225°, $[\alpha]_D^{20} = +7°$ (c=0.5 in water), $\epsilon_{218} = 14250$.

EXAMPLE 29

In analogy to Example 28, there was prepared:
p-[(R)-3-Bis[[(RS)-2-hydroxy-3-phenoxypropyl]amino]-butyl]benzylamine, amorphous, $[\alpha]_D^{20} = -19°$ (c=1.0 in methanol), $\epsilon_{220} = 21010$.

EXAMPLE 30

A solution of 1.0 g of methyl (E)-p-[(R)-2-[[(RS)-2-hydroxy-3-phenoxypropyl]amino]propyl]-β-methyl-cinnamate in 50 ml of tetrahydrofuran was added dropwise while stirring to a mixture of 0.5 g of lithiumaluminumhydride and 50 ml of absolute tetrahydrofuran. The mixture was then heated to reflux for 90 minutes, cooled, treated cautiously with 20 ml of moist ether and subsequently with 2 ml of sodium sulfate. The precipitate was removed by filtration under suction and the filtrate was evaporated in vacuo, whereby there was obtained 1.0 g of a colorless oil which, after chromatography on 50 g of silica gel with chloroform/n-propanol/saturated ammonia (1000:100:5), yielded 650 mg of pure, amorphous (RS)-3-[p-[(R)-2-[[(RS)-2-hydroxy-3-phenoxypropyl]amino]propyl]phenyl]-1-butanol, $[\alpha]_D^{20} = -20°$ (c=0.6 in methanol), $\epsilon_{218} = 16800$.

EXAMPLE 31

0.5 g of p-[(R)-3-[[(RS)-2-hydroxy-3-phenoxypropyl]amino]butyl]benzamide was warmed to 40° for 24 hours in 25 ml of acetic acid saturated with hydrochloric acid gas. Thereupon, the solvent was removed in vacuo and the crystalline residue was recrystallized from acetonitrile, and there was obtained p-[(R)-3-[[(RS)-2-acetoxy-3-phenoxypropyl]amino]butyl]-benzamide hydrochloride of m.p. 83°–85°, $[\alpha]_D^{20} = +10°$ (c=0.6 in methanol), $\epsilon_{222} = 15020$, $\epsilon_{234} = 13590$.

EXAMPLE 32

Analogously to Example 23, there were prepared:
a) p-[(R)-2-[[(S)-2-Hydroxy-3-phenoxypropyl]amino]propyl]phenol, m.p. 107°–108°; $[\alpha]_D^{20} = -28°$ (c=1.0 in methanol); $\epsilon_{221} = 15810$; and
b) p-[(R)-2-[bis[(S)-2-hydroxy-3-phenoxypropyl]amino]propyl]phenol; amorphours $[\alpha]_D^{20} = -5.5°$ (c=1.0 in methanol); $\epsilon_{221} = 20850$.

EXAMPLE 33

After the addition of 100 mg of 10% palladium on carbon, a solution of 600 mg of methyl p-[(R)-2-[[(S)-2-hydroxy-3-phenoxy-propyl]amino]propyl]-β-methyl-cinnamate in 50 ml of ethanol was hydrogenated with hydrogen at normal pressure until one equivalent of hydrogen had been taken up. The catalyst was removed by filtration and the solvent was evaporated in vacuo. There was obtained pure, amorphous methyl (RS)-p-[(R)-2-[[(S)-2-hydroxy-3-phenoxypropyl]amino]propyl]-β-methyl-hydrocinnamate, $[\alpha]_D^{20} = -21°$ (c=1.0 in methanol), $\epsilon_{218} = 17240$.

EXAMPLE 34

Analogously to Example 33, there was prepared:
Methyl (RS)-p-[(R)-2-[bis[(RS)-2-hydroxy-3-phenoxypropyl]amino]propyl-β-methyl-hydrocinnamate, amorphous, $[\alpha]_D^{20} = -24°$ (c=1.0 in methanol); $\epsilon_{219} = 24650$.

EXAMPLE 35

A mixture of 1.0 g of p-[2-[[(RS)-2-hydroxy-3-phenoxypropyl]amino]ethyl]phenol, 487 mg of potassium hydroxide, 1.02 g of 1-(2-phenethoxy)-2-mesyloxyethane and 20 ml of n-propanol was heated to 120° for 22 hours. The reaction mixture was poured on to ice-water and extracted with ethyl acetate. The organic extract was washed with water, dried and evaporated in vacuo. The residue was chromatographed on 80 g of silica gel. Utilizing chloroform/n-propanol/saturated ammonia (500:10:1) there were obtained 700 mg of pure (RS)-1-[[3-[p-[2-(phenethoxy)ethoxy]phenyl]propyl]amino]-3-phenoxy-2-propanol, m.p. 76°–78° (from acetone-hexane), $\epsilon_{220} = 18760$.

EXAMPLE 36

In analogy to Example 35, there were prepared:
a) (S)-1-[[(R)-α-Methyl-p-[2-(phenethoxy)ethoxy]phenethyl]amino]-3-phenoxy-2-propanol, amorphous $[\alpha]_D^{20} = -22°$ (c=0.7 in MeOH), $\epsilon_{222} = 18750$;
b) 1,1'-[[(R)-α-methyl-p-[2-(phenethoxy)ethoxy]phenethyl]imino]bis[(S)-3-phenoxy-2-propanol], amorphous, $[\alpha]_D^{20} = -5°$ (c=0.7 in methanol), $\epsilon_{217} = 26900$.

EXAMPLE 37

300 ml of 6-chlorohexanol were added to a solution of 602 mg of p-[(R)-2-[[(S)-2-hydroxy-3-phenoxypropyl]amino]propyl]phenol and 246 mg of potassium t-butylate in 10 ml of dimethylsulfoxide and the reaction mixture was stirred at 80° for 1 hour. The reaction mixture was evaporated in a high vacuum and the residue was chromatographed on silica gel with chloroform/n-propanol/saturated ammonia (1000:50:3), whereby there were obtained 500 mg of pure, amorphous 6-[p-[(R)-2-[[(S)-2-hydroxy-3-phenoxypropyl]amino]propyl]phenoxy]hexanol, $[\alpha]_D^{20} = -21°$ (c=0.9 in methanol), $\epsilon_{222} = 17230$.

EXAMPLE 38

In analogy to Example 37, there was obtained from p-[(R)-2-[bis-[(S)-2-hydroxy-3-phenoxypropyl]amino]propyl]phenol:
6-[p-[(R)-[Bis[(S)-2-hydroxy-3-phenoxypropyl]amino]propyl]phenoxy]-1-hexanol as an amorphous substance, $[\alpha]_D^{20} = +8°$ (c=1.0 in methanol), $\epsilon_{221} = 25020$.

EXAMPLE 39

525 mg of ethyl 4-bromobutyrate were added to a solution of 574 mg of p-[2-[[(RS)-2-hydroxy-3-phenoxypropyl]amino]ethyl]phenol and 300 mg of potassium t-butylate in 10 ml of dimethylsulfoxide and the mixture was stirred at room temperature under argon for 6 hours. The solvent was evaporated in vacuo and the residue was chromatographed on 75 g of silica gel. Uitlizing chloroform/n-propanol/saturate ammonia (500:10:1), there were obtained 600 mg of pure, amorphous ethyl 4-[p-[2-[[(RS)-2-hydroxy-3-phenoxypropyl]amino]ethyl]phenoxy]butyrate, $\epsilon_{221} = 17510$.

EXAMPLE 40

Analogously to Example 23, there was obtained starting from (S)-phenyl glycidyl ether and methyl 6-[p-[(R)-2-aminopropyl]phenyl]-5-heptenecarboxylate:
Methyl 6-[p-[(R)-2-[[(S)-2-hydroxy-3-phenoxypropyl]amino]propyl]phenyl]-5-heptenecarboxylate, amorphous, $[\alpha]_D^{20} = -21°$ (c=0.5 in methanol), $\epsilon_{248}$ 11090.

The amine starting material was obtained starting from 4-[(R)-2-acetylaminopropyl]acetophenone and 5-carboxypentyltriphenylphosphonium bromide via 6-[p-[(R)-2-acetylaminopropyl]phenyl]-5-heptenecarboxylic acid.

EXAMPLE 41

In analogy to Example 35, there was obtained using 2-mesyloxyethoxyethane:
(S)-1-[[(R)-α-Methyl-p-[2-(ethoxy)ethoxy]phenethyl]amino]-3-phenoxypropanol, amorphous, $[\alpha]_D^{20} = -22°$ (c=0.5 in methanol), $\epsilon_{222} = 17670$.

EXAMPLE 42

In analogy to Example 39, there was obtained using methyl bromoacetate:
Methyl 2-p-[2-[[(RS)-2-hydroxy-3-phenoxypropyl]amino]propyl]phenoxy]acetate, amorphous, $[\alpha]_D^{20} = -39°$ (c=0.8 in methanol), $\epsilon_{220} = 18840$.

EXAMPLE 43

A solution of 1.0 g of p-[2-[bis[(RS)-2-hydroxy-3-phenoxypropyl]amino]ethyl]phenol, 0.27 ml of benzyl bromide and 257 mg of potassium hydroxide in 30 ml of n-propanol was heated to 120° for 18 hours. The reaction mixture was poured on to ice-water and extracted with ethyl acetate. The crude product obtained after evaporation of the solvent was chromatographed on silica gel. The fractions which were uniform according to thin-layer chromatography were recrystallized from acetone-hexane and yielded pure 1,1'-[[p-(benzyloxy)-phenethyl]imino]bis[(RS)-3-phenoxy-2-propanol], m.p. 106°–110°, $\epsilon_{219} = 30020$.

EXAMPLE 44

A mixture of 0.5 g of p-[(R)-2-[[(RS)-2-hydroxy-3-phenoxypropyl]amino]propyl]phenol, 185 mg of potassium hydroxide, 410 mg of 1-(2-chloroethyl)-4-phenyl-piperazine and 15 ml of n-propanol was heated to 60° for 2.5 hours. The reaction mixture was poured on to ice-water and extracted with ethyl acetate. After evaporation of the solvent and chromatography of the crude product on silica gel with chloroform/n-propanol/-saturated ammonia (1000:10:1) there were obtained 340 mg of pure, amorphous (S)-1-[[(R)-α-methyl-p-[2-(4-phenyl-1-piperazinyl)ethoxy]phenethyl]amino]-3-phenoxy-2-propanol, $[\alpha]_D^{20} = -19°$ (c=0.8 in methanol), $\epsilon_{222} = 21890$.

EXAMPLE 45

A solution of 685 mg of p-[(R)-3-[[(R)-2-hydroxy-3-phenoxypropyl]amino]butyl]benzamide and 550 mg of phenacetyl chloride in 10 ml of dioxane saturated with hydrochloric acid was stirred at room temperature for 28 hours. For the working-up, the mixture was poured on to ice-water and extracted with ether. The acidic aqueous solution was treated with sodium hydroxide solution to pH 10 and then extracted with ethyl acetate. The crude product obtained after evaporation of the solvent was chromatographed on silica gel. Utilizing chloroform/n-propanol/saturated ammonia (200:10:1), there was eluted pure (RS)-2-[[(R)-3-(p-carbamoyl-phenyl)-1-methylpropyl]amino]-1-phenoxymethyl-phenyl acetate, amorphous, $[\alpha]_D^{20} = -5°$ (c=0.5 in methanol), $\epsilon_{234} = 13500$.

EXAMPLE 46

400 mg of methyl p-[(R)-2-[[(RS)-2-hydroxy-3-phenoxypropyl]amino]propyl]benzoate were heated to 50° for 4 hours while stirring in 25 ml of 5% methanolic potassium hydroxide solution and 2.5 ml of water. The reaction mixture was cooled, treated with ice-water and extracted with ether. The aqueous, alkaline solution was then acidified to pH 2 with dilute hydrochloric acid and evaporated to dryness in vacuo. The solid residue was freed from water by the repeated addition and evaporation of toluene. The residue, dried at 60° in a high vacuum, was then extracted with 10 ml of hot absolute ethanol, the alcoholic solution was filtered and evaporated in vacuo. The product was freed from hydrochloric acid by repeated recrystallization from absolute ethanol. There was thus obtained pure p-[(R)-2-[[(RS)-2-hydroxy-3-phenoxypropyl]amino]propyl]benzoic acid hydrochloride as a colorless foam, $[\alpha]_D^{20} = -11°$ (c=1.0 in methanol), $\epsilon_{234} = 17500$.

EXAMPLE 47

Analogously to Example 29, there was prepared: (RS)-1-[[(RS)-3-[5-(Aminomethyl)-2-thienyl]-1-methylpropyl]amino]-3-phenoxy-2-propanol, $\epsilon_{221} = 11380$, $\epsilon_{240} = 8600$, $\epsilon_{270} = 1700$, $\epsilon_{277} = 1450$.

EXAMPLE 48

In analogy to Example 9, there was prepared from 2,3-epoxypropyl phenyl ether and 5-(3-aminopropyl)-n-butyl-2-thiophenecarboxamide:
5-[3-[[(RS)-2-Hydroxy-3-phenoxypropyl]amino]-propyl]-n-butyl-2-thiophenecarboxamide, m.p. 110° (acetonitrile).

The starting material is obtained from 5-(3-aminopropyl)-2-thiophenecarboxamide by protecting the free amino group as the 2,5-dimethylpyrrole derivative, butylating the amide group and then cleaving the 2,5-dimethylpyrrole group.

EXAMPLE 49

In analogy to Example 5, from 5-(3-aminopropyl)-N-butyl-2-thiophenecarboxamide and 2,3-epoxypropyl phenyl ether there was obtained 5-[3-[bis-[(RS)-2-hydroxy-3-phenoxypropyl]amino]propyl]-N-butyl-2-thiophenecarboxamide, $\epsilon_{271} = 13540$, $\epsilon_{277} = 13780$.

The starting material can be prepared as follows:
5-(3-Aminopropyl)-2-thiophenecarboxamide is reacted with acetonylacetone to give 5-[3-(2,5-dimethyl-pyrrol-1-yl)propyl]-2-thiophenecarboxamide, m.p. 144°–146° C. (see J. Chem. Soc. Chem. Commun. 800 [1982]). This is alkylated with n-butyl bromide to give N-butyl-5-[3-(2,5-dimethylpyrrol-1-yl)propyl]-2-thio-phenecarboxamide (see Synthesis 266 [1976]). The latter is cleaved with hydroxylamine hydrochloride to give 5-(3-aminopropyl)-N-butyl-2-thiophenecarboxamide.

EXAMPLE 50

(RS)-1-Phenoxy-3-(p-phenoxyphenethylamino)-2-propanol, $\epsilon_{219} = 20510$, was prepared in analogy to Example 9.

EXAMPLE 51

In analogy to Example 5, from p-[(R)-3-aminobutyl]-N-butylbenzamide and 2,3-epoxypropyl phenyl ether, there was obtained p-[(R)-3-[bis[(RS)-2-hydroxy-3-phenoxypropyl]amino]butyl]-N-butylbenzamide, $[\alpha]_D = -18°$ (0.1% in methanol).

The starting material was prepared from p-[(R)-3-aminobutyl]benzamide in analogy to the method described in Example 49 for the preparation of the starting material.

EXAMPLE 52

In analogy to Example 9, from 2,3-epoxypropyl phenyl ether and p-[(R)-3-aminobutyl]-N-butylbenza-mide, there was obtained p-[(R)-3-[[(RS)-2-hydroxy-3-phenoxypropyl]-amino]butyl]-N-butylbenzamide, $[\alpha]_D = +5°$ (0.1% in methanol).

EXAMPLE 53

In analogy to Example 5, from 5-(3-aminopropyl)-N,N-dibutyl-2-thiophenecarboxamide and 2,3-epoxypropyl phenyl ether, there was obtained 5-[3-[bis-[(RS)-2-hydroxy-3-phenoxypropyl]amino]propyl]-N,N-dibutyl-2-thiophenecarboxamide, $\epsilon_{220} = 24420$, $\epsilon_{244} = 9200$, $\epsilon_{271} = 12040$, $\epsilon_{277} = 11530$.

The starting material was prepared from 5-(3-aminopropyl)-2-thiophenecarboxamide in analogy to the method described in Example 49 for the preparation of the starting material.

EXAMPLE 54

In analogy to Example 9, from 2,3-epoxypropyl phenyl ether and 5-(3-aminopropyl)-N,N-dibutyl-2-thiophenecarboxamide, there was obtained 5-[3-[[(RS)-2-hydroxy-3-phenoxypropyl]amino]propyl]-N,N-dibutyl-2-thiophenecarboxamide, $\epsilon_{219}=13150$, $\epsilon_{244}=9260$, $\epsilon_{270}=10240$, $\epsilon_{276}=9960$.

EXAMPLE 55

2.1 g of p-[[(R)-3-[(RS)-2-hydroxy-3-phenoxypropyl]-amino]butyl]-N-butylbenzamide in 92 ml of tetrahydrofuran were treated portionwise with 920 mg of lithiumaluminumhydride and boiled at reflux for 4 hours. The reaction mixture was decomposed with 25 ml of 2N sodium hydroxide, diluted with water and extracted three times with methylene chloride. The methylene chloride solutions were washed twice with water, dried and evaporated in vacuo. There were obtained 2.06 g of (RS)-1-[[(R)-3-[α-(butylamino)-p-tolyl]-1-methylpropyl]-amino]-3-phenoxy-2-propanol, $[\alpha]_{365}=+6°$ (0.1% in MeOH).

EXAMPLE 56

In analogy to Example 55, from 5-[3-[bis-[(RS)-2-hydroxy-3-phenoxypropyl]amino]propyl]-N-butyl-2-thiophenecarboxamide there was obtained 1,1'-[[3-[5-[(butylamino)methyl]-2-thienyl]propyl]imino]bis[(RS)-3-phenoxy-2-propanol], $\epsilon_{220}=20120$, $\epsilon_{241}=9090$, $\epsilon_{270}=3350$, $\epsilon_{277}=2800$.

EXAMPLE 57

A solution of 1.79 g of 5-[3-[[(RS)-2-hydroxy-2-phenoxypropyl]amino]propyl]-N,N-dibutyl-2-thiophenecarboxamide in 28 ml of tetrahydrofuran was added dropwise at 25° in 20 minutes to a suspension of 760 mg of lithiumaluminumhydride in 60 ml of tetrahydrofuran and the mixture was stirred at 25° for an additional 2.5 hours. The working-up was carried out as in Example 55 and gave 1.73 g of (RS)-1-[[3-[5-[(dibutylamino)methyl]-2-thienyl]propyl]amino]-3-phenoxy-2-propanol, $\epsilon_{220}=13050$, $\epsilon_{240}=9350$, $\epsilon_{270}=1950$, $\epsilon_{277}=1560$.

EXAMPLE 58

In analogy to Example 57, from 5-[3-[bis[(RS)-2-hydroxy-3-phenoxypropyl]amino]propyl]-N,N-dibutyl-2-thiophenecarboxamide there was obtained 1,1'-[[3-[5-[(dibutylamino)methyl]-2-thienyl]propyl]imino]-bis[(RS)-3-phenoxy-2-propanol], $\epsilon_{220}=22680$, $\epsilon_{240}=9400$, $\epsilon_{270}=3640$, $\epsilon_{277}=2910$.

EXAMPLE 59

5-[(RS)-2-[Bis-[(RS)-2-hydroxy-3-phenoxypropyl]amino]propyl]-2-thiophenecarboxamide, $\epsilon_{220}=32320$, $\epsilon_{271}=11280$, $\epsilon_{277}=11370$, was prepared in analogy to Example 5.

EXAMPLE 60

1,1'-[[(RS)-2-[5-(Aminomethyl)-2-thienyl]-1-methylethyl]imino]bis[(RS)-3-phenoxy-2-propanol], $\epsilon_{220}=19200$, $\epsilon_{242}=7770$, $\epsilon_{271}=3750$, $\epsilon_{277}=3070$, was prepared in analogy to Example 55.

EXAMPLE 61

Tablets of the following composition were prepared in the usual manner:

| | |
|---|---|
| Active ingredient, for example, methyl E-p-[(R)-2-[bis[(RS)-2-hydroxy-3-phenoxypropyl]amino]propyl]-β-methyl-cinnamate | 250 mg |
| Lactose | 200 mg |
| Maize starch | 300 mg |
| Maize starch paste | 50 mg |
| Calcium stearate | 5 mg |
| Dicalcium phosphate | 45 mg |

We claim:

1. A phenoxypropanolamine of the formula

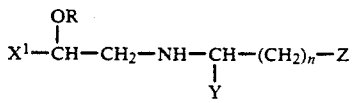

V-1 wherein
n is the integer 1 or 2,
R is hydrogen, lower-alkanoyl or phenyl-lower-alkanoyl,
$X^1$ is phenoxymethyl optionally mono-fluorinated or mono-chlorinated in the ortho-position,
Y is hydrogen or methyl,
Z is a group of the formula

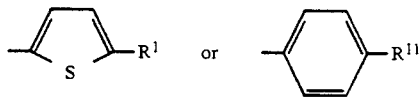

$R^1$ is aminomethyl, N-mono-lower-alkylaminomethyl, N-dilower-alkylaminomethyl or $-C(O)R^2$, $-C(R^3)=CH-(CH_2)_m-C(O)R^2$, $-C(H,R^3)-(CH_2)_{m+1}C(O)R^2$, $-C(H,R^3)-(CH_2)_p-OH$ or $-C(R^3)=CH-C(CH_3)=CH-COOCH_3$, $R^{11}$ is lower-alkanoyloxy, sulfamoyl, benzyloxy or phenoxy optionally ring-substituted by fluorine, chlorine, trifluoromethyl, lower alkyl, lower-alkoxy, or a group $R^1$, $-O-(CH_2)_q-OH$, $-O-(CH_2)_q-O-(CH_2)_r-R^5$ or

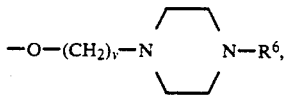

$R^2$ is hydroxy, lower-alkyl, lower-alkoxy, dimethylaminoethoxy, lower-alkoxycarbonylethyl, amino, mono-lower alkylamino or di-lower alkylamino,
$R^3$ is hydrogen or methyl,
$R^4$ is lower-alkyl,
$R^5$ is hydrogen, lower-alkyl or phenyl,
$R^6$ is lower-alkyl or phenyl optionally para-substituted by fluorine, chlorine, lower-alkyl or lower-alkoxy,
m and p are, independently, an integer of 0 to 6,
v is an integer of 2 to 4,
q and t are, independently, an integer of 1 to 6,
an enantiomer thereof, or when Y is methyl a diastereomer thereof, or a physiologically compatible salt thereof.

2. A compound, in accordance to claim 1, wherein $R^{11}$ is lower-alkanoyloxy, sulfamoyl, Aminomethyl, N-mono-lower-alkylaminomethyl, N-di-lower-alkylaminomethyl or —C(O)R², —C(R³)=CH—(CH₂)ₘ—C(O)R², —C(H,R³)—(CH₂)ₘ₊₁C(O)R², —C(H,R³)—(CH₂)ₚ—OH or —C(R³)=CH—C(CH₃)=CH—COOCH₃, —O—(CH₂)_q—OH or —O—(CH₂)_q—O—(CH₂)_r—R⁵ and R⁵ is hydrogen, lower-alkyl or phenyl.

3. A compound, in accordance with claim 2, wherein R is hydrogen.

4. A compound, in accordance with claim 3, wherein X¹ is phenoxymethyl and the C-atom bonded to a phenoxymethyl residue X¹ has the S-configuration.

5. A compound, in accordance with claim 4, wherein Y is methyl, and the C-atom bonded to a methyl residue Y has the R-configuration.

6. A compound of the formula, (S)-1-[[(R)-α-methyl-p-[2-(ethoxy) ethoxy]phenethyl]amino]-3-phenoxy-propanol.

7. A compound selected from the group consisting of methoxy (E)-p-[(R)-2-[[(RS)-2-hydroxy-3-phenoxypropyl]amino]propyl]-β-methyl-cinnamate, p-[(R)-3-[[(RS)-2-hydroxy-3-phenoxypropyl]amino]butyl]benzamide, methyl p-[(R)-2-[[(RS)-2-hydroxy-3-phenoxypropyl]amino]propyl]benzoate, p-[(R)-2-[[(S)-2-hydroxy-3-phenoxypropyl]amino]propyl]phenol, and 6-[p-[(R)-2-[[(S)-2-hydroxy-3-phenoxypropyl]amino]propyl]phenoxy]hexanol.

8. A pharmaceutical composition which comprises an effective amount of a phenoxypropanolamine of the formula

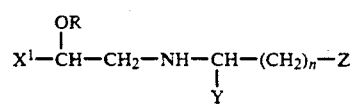   V-1 wherein n is the integer 1 or 2, R is hydrogen, lower-alkanoyl or phenyl-lower alkanoyl, X¹ is phenoxymethyl optionally monofluorinated or mono-chlorinated in the ortho-position, Y is hydrogen or methyl, Z is a group of the formula

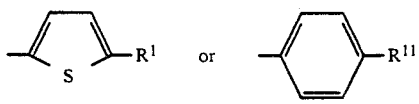

R¹ is aminomethyl, N-mono-lower-alkylaminomethyl, N-di-lower-alkylamino methyl or —C(O)R², —C(R³)=CH—(CH₂)ₘ—C(O)R², —C(H,R³)—(CH₂)ₘ₊₁C(O)R², —C(H,R³)—(CH₂)ₚ—OH or —C(R³)=CH—C(CH₃)=CH—COOCH₃, R¹¹ is lower-alkanoyloxy, sulfamoyl, benzyloxy or phenoxy optionally ring-substituted by fluorine, chlorine, trifluoromethyl, lower alkyl, lower-alkoxy, or a group R¹, —O—(CH₂)_q—OH, [—O—(CH₂)_q—COOR⁴] —O—(CH₂)_q—O—(CH₂)_r—R⁵ or

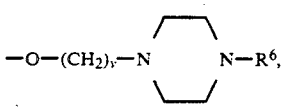

R² is hydroxy, lower-alkyl, lower-alkoxy, dimethylaminoethoxy, lower-alkoxycarbonylethyl, amino, mono-lower-alkylamino or di-lower-alkylamino, R³ is hydrogen or methyl, R⁴ is lower alkyl, R⁵ is hydrogen, lower-alkyl or phenyl, R⁶ is lower-alkyl or phenyl optionally para-substituted by fluorine, chlorine, lower-alkyl or lower-alkoxy, m and p are independently, an integer of 0 to 6, v is an integer of 2 to 4, q and t are, independently, an integer of 1 to 6, an enantiomer thereof, or when Y is methyl a diastereomer thereof, or a physiologically compatible salt thereof, and an inert carrier.

9. A pharmaceutical composition, in accordance with claim 8, wherein R is hydrogen.

10. A pharmaceutical composition in accordance with claim 8, wherein R¹¹ is lower-alkanoyloxy, sulfamoyl, aminomethyl, N-mono-lower-alkyl-aminomethyl, N-di-lower-alkylaminoethyl or C(O)R², —C(R³)=CH—(CH₂)ₘ—C(O)R², —C(H,R³)—(CH₂)ₘ₊₁C(O)R², —C(H,R³)—(CH₂)ₚ—OH or —C(R₃)=CH—C(CH₃)=CH—COOCH₃, —O—(CH₂)_q—OH or —O—(CH₂)_q—O—(CH₂)_r—R⁵ and R⁵ is hydrogen, lower-alkyl or phenyl.

11. A pharmaceutical composition in accordance with claim 8, wherein the compound of formula V-1 is (S)-1-[[(R)-α-methyl-p-[2-(ethoxy)]phenylethyl]amino]-3-phenoxypropanol.

* * * * *